United States Patent
Proksa et al.

(10) Patent No.: US 10,269,146 B2
(45) Date of Patent: Apr. 23, 2019

(54) IMAGE DATA SEGMENTATION AND DISPLAY

(71) Applicant: KONINKLIJKE PHILIPS N.V., Eindhoven (NL)

(72) Inventors: Roland Proksa, Neu Wulmstorf (DE); Rafael Wiemker, Kisdorf (DE); Liran Goshen, Pardes-Hanna (IL); Shlomo Gotman, Haifa (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 15 days.

(21) Appl. No.: 15/544,092

(22) PCT Filed: Dec. 30, 2015

(86) PCT No.: PCT/IB2015/060040
§ 371 (c)(1),
(2) Date: Jul. 17, 2017

(87) PCT Pub. No.: WO2016/116795
PCT Pub. Date: Jul. 28, 2016

(65) Prior Publication Data
US 2018/0012382 A1 Jan. 11, 2018

Related U.S. Application Data

(60) Provisional application No. 62/105,377, filed on Jan. 20, 2015.

(51) Int. Cl.
*G06T 7/00* (2017.01)
*G06T 11/00* (2006.01)
(Continued)

(52) U.S. Cl.
CPC .............. *G06T 11/003* (2013.01); *G06F 3/14* (2013.01); *G06T 7/0012* (2013.01); *G06T 7/11* (2017.01);
(Continued)

(58) Field of Classification Search
None
See application file for complete search history.

(56) References Cited

U.S. PATENT DOCUMENTS 6,999,549 B2  2/2006  Sabol
7,796,795 B2  9/2010  Uppaluri
(Continued)

FOREIGN PATENT DOCUMENTS

EP  2405260  1/2012
EP  2437050  4/2012
(Continued)

*Primary Examiner* — Tahmina N Ansari (57) ABSTRACT

A method displays spectral image data reconstructed from spectral projection data with a first reconstruction algorithm and segmented image data reconstructed from the same spectral projection data with a different reconstruction algorithm, which is different from the first reconstruction algorithm. The method includes reconstructing spectral projection data with the first reconstruction algorithm, which generates the spectral image data and displaying the spectral image data. The method further includes reconstructing the spectral projection data with the different reconstruction algorithm, which generates segmentation image data, segmenting the segmentation image data, which produces the segmented image data, and displaying the segmented image data.

20 Claims, 5 Drawing Sheets

(51) Int. Cl.
*G06T 7/11* (2017.01)
*G06F 3/14* (2006.01)
*G06T 11/60* (2006.01)

(52) U.S. Cl.
CPC ............ *G06T 11/008* (2013.01); *G06T 11/60* (2013.01); *G06T 2207/10081* (2013.01); *G06T 2211/408* (2013.01)

(56) References Cited

U.S. PATENT DOCUMENTS

| | | |
|---|---|---|
| 8,115,784 B2 | 2/2012 | Licato |
| 2004/0101104 A1 | 5/2004 | Avinash |
| 2009/0122953 A1* | 5/2009 | Imai ................. A61B 6/032 378/5 |
| 2010/0310036 A1 | 12/2010 | Burleton |
| 2011/0150183 A1* | 6/2011 | Wu ................... A61B 6/032 378/98.9 |
| 2015/0103971 A1* | 4/2015 | Chen ................. A61B 6/482 378/5 |
| 2017/0109904 A1* | 4/2017 | Huang ............... G06T 11/008 |
| 2018/0012382 A1* | 1/2018 | Proksa ............... G06T 11/008 |

FOREIGN PATENT DOCUMENTS

| | | |
|---|---|---|
| WO | 2008/047270 | 4/2008 |
| WO | 2013/165396 | 11/2013 |
| WO | 2015/059613 | 4/2015 |

\* cited by examiner

IMAGE DATA SEGMENTATION AND DISPLAY

CROSS REFERENCE TO RELATED APPLICATIONS

This application is the U.S. National Phase application under 35 U.S.C. § 371 of International Application No. PCT/I132015/060040, filed Dec. 30, 2015, published as WO 2016/116795 on Jul. 28, 2016, which claims the benefit of U.S. Provisional Patent Application No. 62/105,377 filed on Jan. 20, 2015. These applications are hereby incorporated by reference herein.

FIELD OF THE INVENTION

The following generally relates to imaging and more particularly to image data segmentation and display, and is described with particular application to computed tomography (CT). However, other imaging modalities with spectral imaging capabilities are also contemplated herein.

BACKGROUND OF THE INVENTION

A CT scanner generally includes an x-ray tube mounted on a rotatable gantry opposite a detector array across an examination region. The rotatable gantry and hence the x-ray tube rotate around the examination region. The x-ray tube emits radiation that traverses the examination region and is detected by the detector array. The detector array generates and outputs a signal indicative of a strength of the detected radiation. The signal is reconstructed to generate volumetric image data.

For reading, a clinician has viewed the volumetric image data using different visualization software applications. One such application includes an image segmentation tool which allows the clinician to segment tissue of interest in the volumetric image data for viewing and/or analysis. The segmentation can be performed manually by a user through the image segmentation tool and/or semi-automatically through a combination of acts by the clinician and the image segmentation tool.

With one example semi-automated image segmentation, a user hovers a mouse pointer over a location on a displayed image to identify a location as a point of interest. The actual location of point of interest is used as a seed or starting point for an automated segmentation. The automated segmentation is performed in the background with the segmentation results immediately shown in a viewport superimposed over the image. This is repeated automatically if the mouse pointer is moved over the image for each location identified by the mouse pointer without requiring any mouse-clicks.

Unfortunately, segmentation performed on the volumetric image data being observed may produce a less than optimal result. For instance, a scan performed with an imaging protocol that smooths the data may render it difficult for the clinician and/or visualization software application to accurately identify a perimeter of tissue of interest. In view of at least the above, there is an unresolved need for other approaches for segmenting tissue of interest.

SUMMARY OF THE INVENTION

Aspects described herein address the above-referenced problems and others.

In one aspect, a method displays spectral image data, which is reconstructed from spectral projection data with a first reconstruction algorithm and segmented image data reconstructed from the same spectral projection data but with a different reconstruction algorithm. The method includes reconstructing spectral projection data with the first reconstruction algorithm. This generates the spectral image data. The method further includes reconstructing the spectral projection data with the different reconstruction algorithm. This generates segmentation image data. The method further includes segmenting the segmentation image data. This produces the segmented image data.

In another aspect, a computing system includes a memory device configured to store instructions, including a segmentation and visualization module. The computing system further includes a processor that executes the instructions. The processor, in response to executing the instructions, reconstructs spectral projection data with the first reconstruction algorithm. This generates spectral image data. The processor reconstructs the spectral projection data with the different reconstruction algorithm. This generates segmentation image data. The processor segments the segmentation image data. This produces segmented image data.

In another aspect, a computer readable storage medium is encoded with computer readable instructions. The computer readable instructions, when executed by a processor, cause the processor to reconstruct spectral projection data with the first reconstruction algorithm. This generates spectral image data. The processor reconstructs the spectral projection data with the different reconstruction algorithm. This generates segmentation image data. The processor segments the segmentation image data. This produces segmented image data.

The invention may take form in various components and arrangements of components, and in various steps and arrangements of steps. The drawings are only for purposes of illustrating the embodiments and are not to be construed as limiting the invention.

DETAILED DESCRIPTION OF EMBODIMENTS

Figure 1:
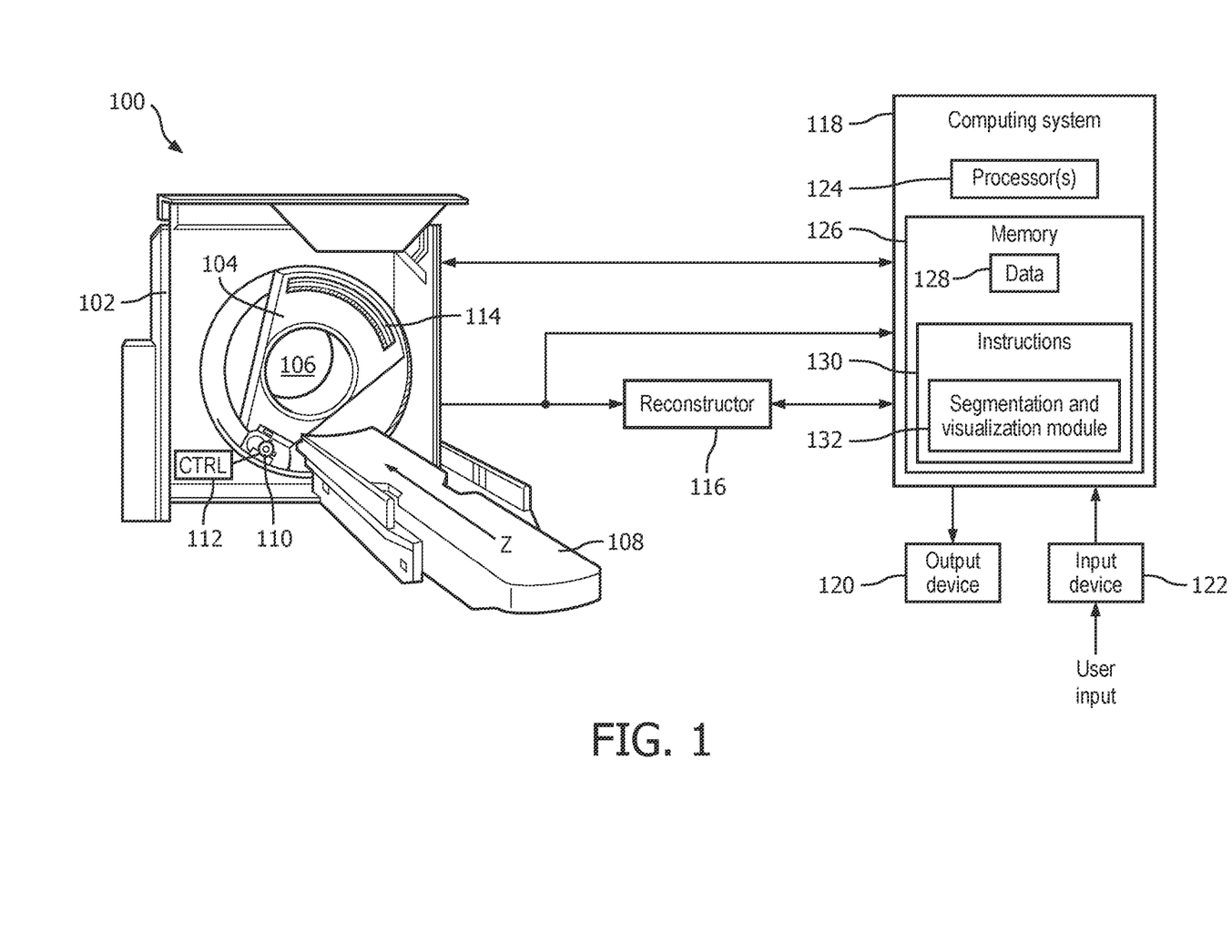
FIG. 1 schematically illustrates an example imaging system with a segmentation and visualization module.

FIG. 1 illustrates an imaging system 100, such as a computed tomography (CT) scanner. The imaging system 100 includes a stationary gantry 102 and a rotating gantry 104, which is rotatably supported by the stationary gantry 102 and rotates around an examination region 106 about a z-axis. A subject support 108, such as a couch, supports an object or subject in the examination region 106. The subject support 108 is configured to translate vertically and/or horizontally and is positionable for object or subject loading, scanning, and/or unloading.

A radiation source 110, such as an x-ray tube, is supported by the rotating gantry 104, rotates with the rotating gantry 104, and emits radiation that traverses the examination region 106. In one instance, a controller (CTRL) 112 controls a mean or peak emission voltage of the radiation source 110, which includes switching the emission voltage between two or more emission voltages (e.g., 80 and 140 kVp, 100 and 120 kVp, etc.) within an integration period and/or otherwise. In a variation, the imaging system 100 includes at least two radiation sources 110, and the controller 112 controls the at least two radiation sources 110 to emit radiation at different emission voltages. In another variation, the radiation source 110 includes a single broad spectrum x-ray tube.

A detector array 114 subtends an angular arc opposite the examination region 106 relative to the radiation source 110. The detector array 114 detects radiation that traverses the examination region 106 and generates projection data indicative thereof. Where the radiation source voltage is switched between at least two emission voltages and/or two or more x-ray tubes emit radiation at two different emission voltages, the detector array 114 generates projection data for each of the radiation source voltages. For a single broad spectrum x-ray tube, the detector array 114 includes an energy-resolving detector (e.g., multi-layered, photon counting, etc.) that produces spectral projection data.

A reconstructor 116 reconstructs the spectral projection data and produces volumetric image data. In one instance, the volumetric image data includes one or more base volumetric image data sets corresponding to one or more different energies. Examples of a base include photoelectric absorption, Compton scatter, virtual non contrast (VNC), relative material (e.g., iodine, K-edge, etc.) concentration, anatomical tissue (e.g., bone, soft tissue, etc.), quasi mono energetic absorption, effective atomic number (Z), Carbon-Oxygen ratio, and/or other base. The reconstructor 116 can also combine the spectral projection data and reconstruct the non-spectral projection data and/or combine the one or more base volumetric image data sets to produce a non-spectral (conventional) volumetric image data set.

A computing system 118 serves as an operator console. The computing system 118 allows an operator to control an operation of the system 100. This includes selecting an imaging acquisition protocol(s), invoking scanning, invoking a visualization software application such as one that includes a segmentation software tool, interacting with an executing visualization software application, etc. The computing system 118 includes at least an output device(s) 120 such as a display monitor, a filmer, etc., an at least one an input device(s) 122 such as a mouse, keyboard, etc. The computing system 118 obtains the spectral projection and/or image data from the system 100 and/or other device.

The computing system 118 further includes at least one processor 124 (e.g., a central processing unit or CPU, a microprocessor, or the like) and a computer readable storage medium ("memory") 126 (which excludes transitory medium), such as physical memory and/or other non-transitory memory. The computer readable storage medium 126 stores data 128 and computer readable instructions 130. The at least one processor 124 executes the computer readable instructions 130 and/or computer readable instructions carried by a signal, carrier wave, and other transitory medium.

The computer readable instructions 130 include at least a segmentation and visualization module 132. As described in greater detail below, the segmentation and visualization module 132, in one instance, visually presents, in a main viewport or window (e.g., a region of a display monitor configured for displaying data), spectral image data generated using a first reconstruction algorithm and segments a region of interest identified therein from segmentation image data generated from the same spectral projection data but with a different reconstruction algorithm, producing segmented image data generated, which can be displayed individually and/or in connection with the spectral image data.

By way of non-limiting example, in one instance the segmentation and visualization module 132 causes the processor 124 to construct and display a virtual non contrast (VNC) image and perform a segmentation of a region of interest identified in the VNC image in an iodine map generated from the same projection or acquisition data, but with a different reconstruction algorithm. Examples of the different reconstruction algorithms include photoelectric absorption, Compton scatter, VNC, relative material (e.g., iodine, K-edge, etc.) concentration, anatomical tissue (e.g., bone, soft tissue, etc.), quasi mono energetic absorption, effective atomic number (Z), Carbon-Oxygen ratio, etc.

Figure 2:
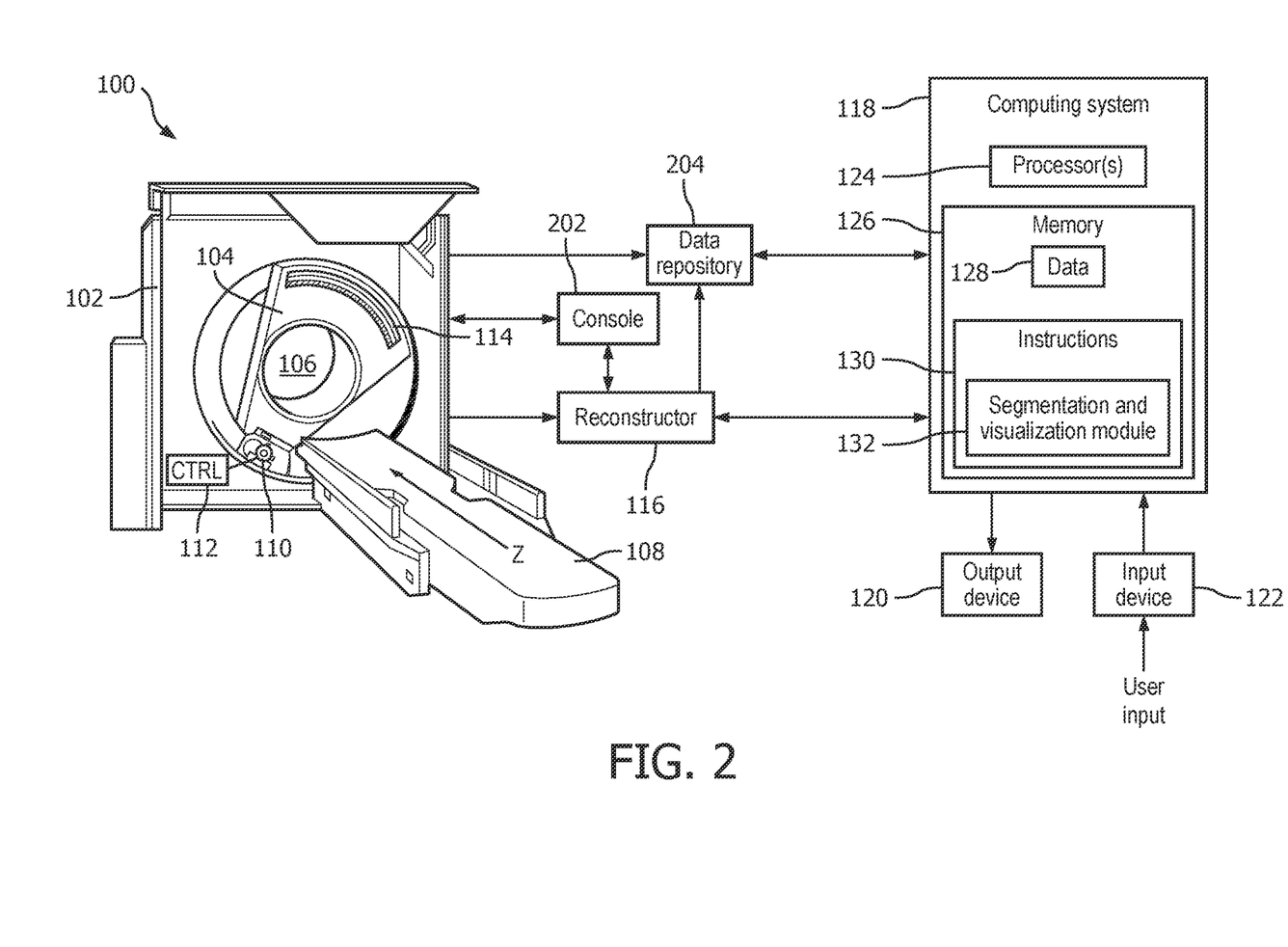
FIG. 2 schematically illustrates an example imaging system in connection with a computing system with the segmentation and visualization module.

FIG. 2 shows a variation of the system 100 of FIG. 1 in which the imaging system 100 includes a console 202 and the computing system 118 is separate from the imaging system 100. The computing system 118 obtains the spectral projection and/or spectral image data from the system 100, a data repository 204, and/or other device. An example of a data repository 204 includes a picture archiving and communication system (PACS), a radiology information system (RIS), a hospital information system (HIS), and an electronic medical record (EMR). The spectral projection and/or spectral image data can be conveyed using formats such as Health Level Seven (HL7), Extensible Markup Language (XML), Digital Imaging and Communications in Medicine (DICOM), and/or one or more other format(s), which may or may not include encryption.

Figure 3:
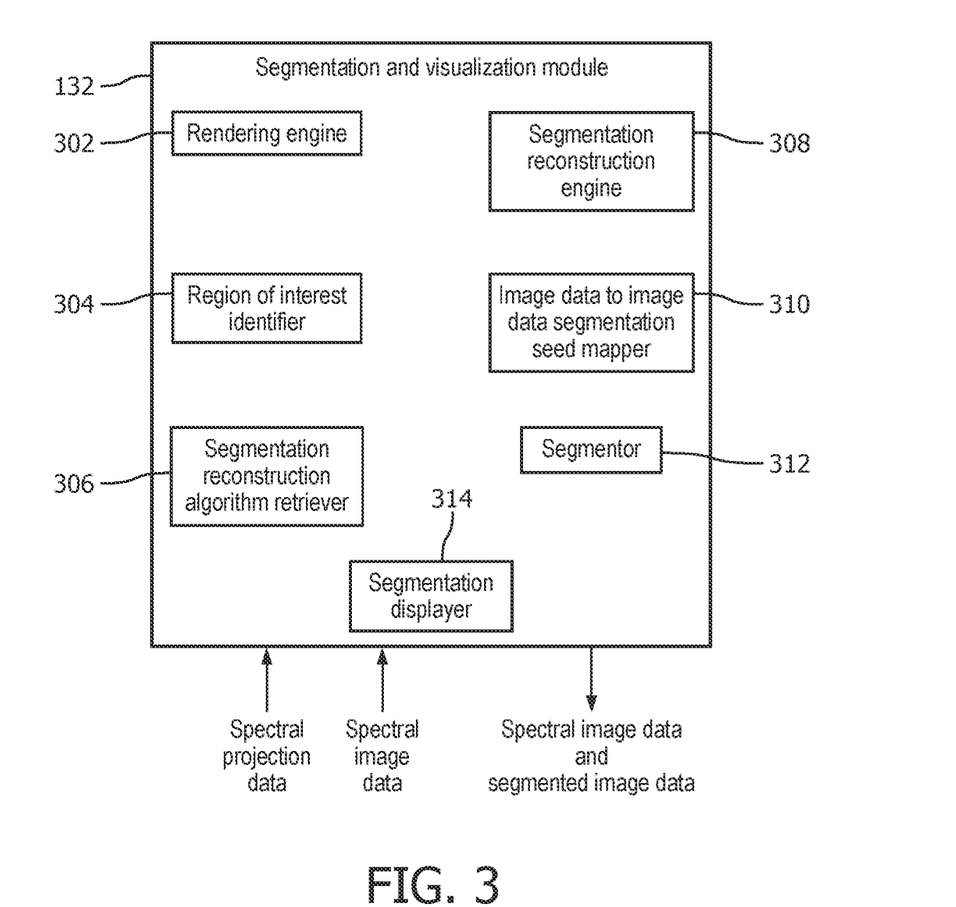
FIG. 3 schematically illustrates an example of the segmentation and visualization module.

FIG. 3 schematically illustrates an example of the segmentation and visualization module 132.

The segmentation and visualization module 132 receives, as input, spectral projection data and/or the spectral image data which is generated by reconstructing the spectral image data. The spectral projection data and/or the spectral image data can be obtained from the imaging system 100, the data repository 204, another imaging system, the memory 126, and/or other device.

A rendering engine 302 displays the spectral image data, for example, in a main view port. The rendering engine 302 may provide a set of GUI tools for manipulating the display of the spectral image data. Such tools may include one or more of a window level/width tool, a pan tool, a zoom tool, a rotate tool, and/or other data manipulation tool(s). This allows the clinician to adjust the displayed view the scanned object or interest.

A region of interest identifier 304 identifies a region of interest for segmentation in the displayed spectral image data. In one instance, this includes receiving a signal indicative of a location of a mouse pointer hovering over the displayed spectral image. The region of interest identifier 304 identifies the location of the mouse pointer as a region of interest segmentation seed for a segmentation region of interest.

A segmentation reconstruction algorithm retriever 306 retrieves a reconstruction algorithm (which is different from the reconstruction algorithm used to reconstruct the spectral image data) that will be used to reconstruct the spectral projection to produce different spectral image data segmentation. This algorithm is referred to herein as a segmentation reconstruction algorithm. The different spectral image data is referred to herein as segmentation image data.

The segmentation reconstruction algorithm can be a default algorithm, based on the imaging protocol (e.g., and identified based on a header or other field in the electronic data file), identified through a signal from the input device 122 indicative of a user selected algorithm, based on the reconstruction algorithm used to reconstruct spectral image data, and/or otherwise identified.

A segmentation reconstruction engine 308 reconstructs the spectral projection data with the segmentation reconstruction algorithm and produces the segmentation image data. Alternatively, the reconstructor 116 (FIG. 1) can be employed to reconstruct the spectral projection data with the segmentation reconstruction algorithm and produce the segmentation image data.

An image data to image data segmentation seed mapper 310 maps the segmentation seed identified in the displayed spectral image data to a corresponding seed point in the segmentation image data. A segmentor 312 segments the segmentation image data using the mapped segmentation seed. For the segmentation, the segmentor 312 can employ known and/or other segmentation algorithms.

A segmentation displayer 314 constructs segmentation image data of the segmented region and displays the constructed segmentation image data, either superimposed or overlaid over a sub-portion of the main viewport or individually in the main viewport or a sub-viewport. With reference to the above example, the displayed spectral image data is the VNC image data, the segmentation image data is the iodine map, and the displayed segmented image data is the segmented region segmented from the segmentation image data.

Figure 4:
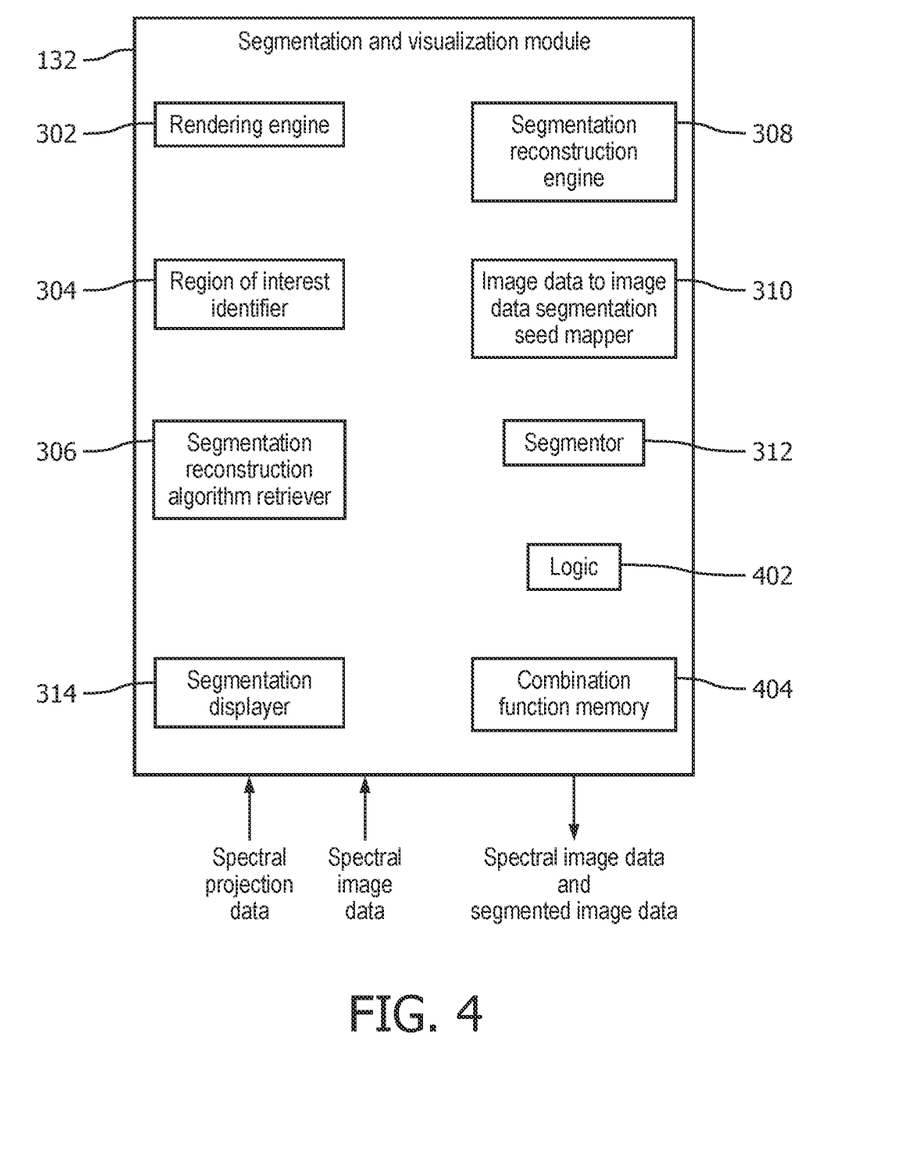
FIG. 4 illustrates a variation of the segmentation and visualization module of FIG. 3.

FIG. 4 schematically illustrates a variation of module 132 of FIG. 3 that further includes logic 402. In this variation, the segmentation reconstruction engine 308 performs multiple different segmentation reconstructions, each using a different segmentation reconstruction algorithm, and produces multiple different sets of segmentation image data for a segmentation. The different reconstructions can be performed in parallel or series.

The segmentation displayer 314 can respectively construct and display segmented image data for each of the multiple different segmentation reconstructions. The results of these segmentations can be visualized individually (e.g. one colored contour plot for each base material segmentation) and/or with combination functions. In this example, the logic 402 implements one or more of the combination functions, which are stored in a combination function memory 404.

An example combination function includes logical "OR", which is used to merge one or more of the multiple different segmented image data sets together (e.g., union). Another example combination function includes logical "AND", which extracts only image points that are inside each of the first and the at least second segmented image data (e.g., intersection). Yet another example combination function includes logical "DIFFERENCE", which extracts only image points that are in the first segmented image data and not inside the at least second segmented image data.

Still another example combination function includes logical "MAX", which utilizes the segmentation contour with a highest gradient. Another example combination function includes multiple sub-combination functions. A non-limiting example includes a complex combination of multiple segmented image data sets combined with multiple combination functions such as "Iodine AND NOT Bone OR K-edge." The combinations may generate multiple isolated regions, which can be visualized individually and/or simultaneously. One other combination functions are also contemplated herein.

In a variation, the logic 402 selects a sub-set of the multiple different segmentation reconstructions. In one instance, this includes selecting only one of the multiple different segmented image data sets, for example, a "most informative' or probable segmentation based on, for example, an entropy of the segmented region and/or other criteria.

In another variation, the image segmentation is based on the sum or square of all gradient magnitudes for each base material image for each pixel.

In another variation, the segmentation seed is provided by an eye tracker, which measures the user's view focus. This approach can be used in addition to or in place of using a current input device (e.g., a mouse cursor, a stylus, a digital pen, actuated touchscreen area, etc.) position to identify the segmentation seed.

In another variation, the segmentation approach described herein can be used in conjunction with other visualization approaches. For example, the segmentation approach described herein can be used with a visualization approach for concurrently displaying multiple views of a same sub-region or anatomical area of image data using a different processing algorithm for each view. An example of such an approach is described in patent application serial number PCT/IB2014/065423, filed 17 Oct. 2014, and entitled "Image Visualization," the entirety of which is incorporated herein by reference.

With the approach described in PCT/IB2014/065423, multiple views of the same region of interest are superimposed over different non-overlapping sub-portions of image data displayed in a main viewport. The different processing algorithms include, but are not limited to, a poly-energetic X-Ray, a mono-energetic X-Ray, a relative material concentration, an effective atomic number, 2D/3D, and/or other processing algorithm. As disclosed in PCT/IB2014/065423, the processing algorithms may enhance image quality and/or increase the visualization of certain tissue/introduced contrast materials.

Figure 5:
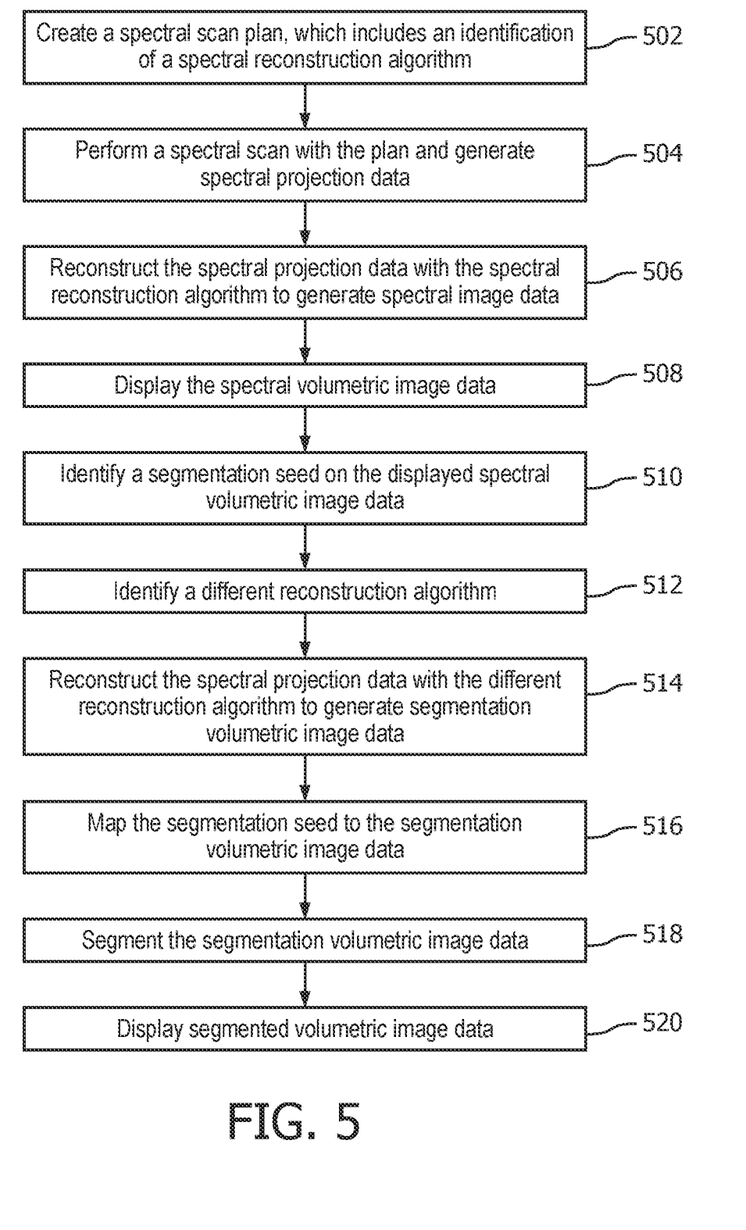
FIG. 5 illustrates a method for displaying image data reconstructed from projection data with one reconstruction algorithm and segmenting image data reconstructed from the same projection data but with a different reconstruction algorithm.

FIG. 5 illustrates a method for displaying image data reconstructed from projection data with one reconstruction algorithm and segmenting image data reconstructed from the projection data with a different reconstruction algorithm.

It is to be appreciated that the ordering of the acts is not limiting. As such, other orderings are contemplated herein. In addition, one or more acts may be omitted and/or one or more additional acts may be included.

At 502, a spectral scan plan, which includes an identification of a spectral reconstruction algorithm of interest, is created.

At 504, a spectral scan is performed, based on the spectral scan plan, which generates spectral projection data.

At 506, the spectral projection data is reconstructed with the spectral reconstruction algorithm of interest, which generates spectral volumetric image data.

At 508, the spectral volumetric image data is visually displayed.

At 510, a segmentation seed is identified in the displayed spectral volumetric image data.

At 512, a different spectral reconstruction algorithm is identified, as described herein and/or described otherwise.

At 514, the different spectral reconstruction algorithm is used to process the spectral projection data and generate segmentation volumetric image data.

At 516, a location of the segmentation seed in the displayed spectral volumetric image data is mapped to the segmentation volumetric image data.

At 518, the segmentation volumetric image data is segmented based on the segmentation seed, producing segmented image data.

At 520, the segmented image data is visually displayed, as described herein and/or described otherwise.

The method herein may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method for displaying spectral image data reconstructed from spectral projection data with a first reconstruction algorithm and segmented image data reconstructed from the same spectral projection data with a different reconstruction algorithm, which is different from the first reconstruction algorithm, comprising:
   reconstructing spectral projection data with the first reconstruction algorithm, which generates the spectral image data;
   displaying the spectral image data;
   reconstructing the spectral projection data with the different reconstruction algorithm, which generates segmentation image data;
   receiving a signal indicative of a user selected location on the displayed spectral image data, wherein the location identifies a point for a segmentation seed;
   mapping the segmentation seed location to a corresponding location on the segmentation image data;
   segmenting the segmentation image data from the segmentation seed location to produce the segmented image data, which is less than all of the segmentation image data; and
   superimposing the segmented image data over a corresponding sub-portion of the displayed spectral image data.

2. The method of claim 1, wherein the first reconstruction algorithm and the different reconstruction algorithm are different spectral reconstruction algorithms.

3. The method of claim 2, wherein the different spectral reconstruction algorithm are selected from a group consisting of photoelectric absorption, Compton scatter, virtual non contrast, relative material concentration, anatomical tissue, quasi mono energetic absorption, effective atomic number or Carbon-Oxygen ratio algorithms.

4. The method of claim 1, further comprising:
   reconstructing the spectral projection data with a second different reconstruction algorithm, which generates second segmentation image data;
   segmenting the second segmentation image data, which produces second segmented image data; and
   displaying the first and the second segmented image data.

5. The method of claim 4, further comprising:
   combining the first and the second segmented image data, which generates combined segmented image data; and
   displaying the combined segmented image data.

6. A computing system, comprising:
   a memory device configured to store instructions, including a segmentation and visualization module; and
   a processor configured to execute the instructions to cause the processor to:
      reconstruct spectral projection data with the first reconstruction algorithm, which generates spectral image data;
      display the spectral image data;
      reconstruct the spectral projection data with the different reconstruction algorithm, which generates segmentation image data;
      receive a segmentation seed location identified by a user on the displayed spectral image data;
      map the segmentation seed location to a corresponding location on the segmentation image data;
      segment the segmentation image data based on the segmentation seed location to produce segmented image data; and
      display the segmented image data.

7. The computing system of claim 6, wherein the first reconstruction algorithm and the different reconstruction algorithm are different spectral reconstruction algorithms.

8. The computing system of claim 6, wherein the segmented image data is superimposed over a sub-portion of the displayed spectral image data.

9. The computing system of claim 6, wherein the segmented image data is displayed individually in an image viewport separate from a viewport displaying the spectral image data.

10. The computing system of claim 6, wherein the processor reconstructs the spectral projection data with a second different reconstruction algorithm that generates second segmentation image data, segments the second segmentation image data that produces second segmented image data, and displays the first and the second segmented image data.

11. The computing system of claim 10, wherein the processor combines the first and the second segmented image data with a combination function, which generates combined segmented image data.

12. A computer readable storage medium encoded with computer readable instructions, which, when executed by a processer, causes the processor to:
   reconstruct spectral projection data with the first reconstruction algorithm, which generates spectral image data;
   display the spectral image data;
   reconstruct the spectral projection data with the different reconstruction algorithm, which generates segmentation image data;
   receive a segmentation seed location identified by a user on the displayed spectral image data;
   map the segmentation seed location to a corresponding location on the segmentation image data;
   segment the segmentation image data based on the segmentation seed location to produce segmented image data; and
   display the segmented image data.

13. The computer readable storage medium of claim 12, wherein the first reconstruction algorithm and the different reconstruction algorithm are different spectral reconstruction algorithms.

14. The computer readable storage medium of claim 12, wherein the computer readable instructions further cause the processor to: superimpose the segmented image data over a sub-portion of the displayed spectral image data.

15. The computer readable storage medium of claim 12, wherein the computer readable instructions further cause the processor to: individually display the segmented image data in an image viewport separate from a viewport displaying the spectral image data.

16. The method of claim 5, further comprising:
combining the first and the second segmented image data with a logic "OR" combination function, which merges the first and the second segmented image data together.

17. The method of claim 5, further comprising:
combining the first and the second segmented image data with a logic "AND" combination function, which extracts only image points that are inside each of the first and the second segmented image data.

18. The method of claim 5, further comprising:
combining the first and the second segmented image data with a logic "DIFFERENCE" combination function, which extracts only image points that are the first segmented image data and not inside the second segmented image data.

19. The method of claim 5, further comprising:
combining the first and the second segmented image data with a logic "MAX" combination function, which utilizes the segmentation contour with a highest gradient.

20. The method of claim 5, further comprising:
selecting one of the first and the second segmented image data based on an entropy of the first and the second segmented image data.

\* \* \* \* \*